United States Patent
Raiden et al.

[11] Patent Number: 5,840,334
[45] Date of Patent: Nov. 24, 1998

[54] SELF-BINDING SHEARFORM COMPOSITIONS

[75] Inventors: Michael G. Raiden, Fairfax; Pradeepkumar P. Sanghvi, Herndon; Tushar K. Misra, Leesburg; Jeffery W. Currington, Winchester; Satish V. Kamath, Centreville, all of Va.; Mahendra Govind Pankhania, Nottingham, England

[73] Assignee: Fuisz Technologies Ltd., Chantilly, Va.

[21] Appl. No.: 915,068

[22] Filed: Aug. 20, 1997

[51] Int. Cl.⁶ ........................................... A61K 9/20
[52] U.S. Cl. ................ 424/464; 424/465; 424/468; 424/469; 424/470; 424/484; 424/488; 424/489; 424/490; 424/493; 424/499
[58] Field of Search ...................... 424/488, 484, 424/489, 490, 493, 499, 464, 465, 468, 469, 470

[56] References Cited

U.S. PATENT DOCUMENTS

| | | | |
|---|---|---|---|
| 5,075,291 | 12/1991 | DuRoss | 514/60 |
| 5,382,601 | 1/1995 | Nurnberg et al. | 424/465 |
| 5,385,749 | 1/1995 | Serpelloni et al. | 426/658 |
| 5,550,292 | 8/1996 | Sakura et al. | 564/399 |
| 5,622,719 | 4/1997 | Meyers et al. | 424/488 |

FOREIGN PATENT DOCUMENTS 0 636 364 A1   1/1995   European Pat. Off. ......... A61K 9/20

*Primary Examiner*—Thurman K. Page
*Assistant Examiner*—Lakshmi S. Channavajjala
*Attorney, Agent, or Firm*—Sandra M. Nolan

[57] ABSTRACT

Shearform compositions made without added glycerine are disclosed. The compositions are self-binding and exhibit excellent cohesivity when used in tableting compositions. Typically, xylitol is incorporated into a feedstock which is flash-flow processed to form a self-binding shearform matrix.

30 Claims, No Drawings

SELF-BINDING SHEARFORM COMPOSITIONS

FIELD OF THE INVENTION

The compositions of the invention have enhanced cohesive and self-binding properties which permit tableting without added glycerine. They contain unique combinations of components, which combinations are processed using flash heat to yield tabletable masses.

BACKGROUND OF THE INVENTION

Glycerine, a tableting additive, has been used for its ability to lend stickiness to tablet formulations. Some stickiness is desirable, serving to provide cohesion to hold the tablet ingredients together so that they are flowable and can be processed readily. However, in certain situations, the use of glycerine can produce too much stickiness, resulting in the formulations clumping or sticking in various machine parts before and during tableting. Self-binding, readily flowable compositions containing no glycerine have been unknown to the art.

One method for addressing the need for self-binding flowable formulations was the production of shearform matrices or flosses. These matrices result when using certain processing techniques, such as the following:

Matrices formed by flash-heat processing are known. U.S. Pat. No. 5,429,836, incorporated herein by reference, describes the flash flow process and its use to make amorphous solid shearform matrices having flake-like form.

U.S. Pat. No. 5,587,172, also incorporated herein by reference, discusses the use of flash heat techniques to produce sucrose-containing flosses, which are then processed to yield tablets.

The use of shearform matrices for forming comestible units is described in co-assigned and co-pending PCT application No. PCT/US95/07144, filed Jun. 6, 1995. The PCT case discloses a quick dissolving tablet which is formed by: (1) using flash-flow technology to provide a shearform matrix; (2) combining the partially recrystallized matrix with an additive to form flowable, compactable particulate blends; and (3) compacting the blends at relatively low pressure to form comestible units, such as tablets.

Additionally, PCT publication WO 95/34293 (published Dec. 21, 1995) from co-assigned PCT Application No. PCT/US95/07194, filed Jun. 6, 1995, discloses a process and apparatus for making rapidly dissolving dosage units by flash-flow processing. In this PCT application, a shearform matrix is formed by the flash-flow process, the shearform matrix is combined with an additive, and the matrix is molded to make a unit dosage form. Tamping may be used to compact the dosage form and increase its integrity.

SUMMARY OF THE INVENTION

The invention provides matrices to be used in compositions having improved tableting properties, compositions containing those matrices and methods of making them.

Applicants have now discovered that, for tablet formulations derived from saccharide-based carriers, the use of a unique combination of carrier or feedstock ingredients yields self-binding, flowable matrices and tablet compositions. This combination—which uses a blend of the sugar alcohols sorbitol and xylitol—is superior to glycerine in providing cohesive properties and flowability. The combination minimizes the incidence of sticking and clumping problems associated with the use of glycerine in compositions to be tableted. Furthermore, tablet compositions containing these sugar alcohols are useful in both high- and low-pressure tableting processes.

The tablet compositions of the invention are based on matrices which comprise xylitol and at least one more sugar alcohol, which matrices fall into one of the following groups of matrix systems:

One group is exemplified by a shearform matrix, or floss, containing a carrier and two or more sugar alcohols, one of which is xylitol. This a "single floss" or "unifloss" system.

A second group is exemplified by (I) a first shearform carrier matrix comprising a carrier and at least one sugar alcohol, generally sorbitol (the "base floss"); and (II) a second shearform binder matrix comprising a carrier and xylitol (the "binder floss"). This is a "dual floss" system.

Actives and other conventional tablet ingredients can be added, in suitable amounts, to the self-binding shearform matrices of the present invention during the production of the matrices and/or after the matrices are collected and chopped, but before tableting.

DETAILED DESCRIPTION OF THE INVENTION

Unless otherwise stated, the parts and percentages used in the specification are weight percentages, based upon total composition weight. The terms "matrix" and "floss" are used interchangeably.

The preparation of flosses suitable for use in the present invention is disclosed in co-assigned patent applications PCT application No. PCT/US95/07144, filed Jun. 6, 1995 and PCT publication WO 95/34293, both incorporated herein by reference. Preferably, the floss is a "shearform matrix" produced by subjecting a feedstock which contains a sugar carrier to flash-heat processing.

In the flash-heat process, the feedstock is simultaneously subjected to centrifugal force and to a temperature gradient which raises the temperature of the mass to create an internal flow condition which permits part of it to move with respect to the rest of the mass. The flowing mass exits through openings provided in the perimeter of a spinning head. The temperature gradient is supplied using heaters or other means which cause the mass' temperature to rise. Centrifugal force in the spinning head flings the internally flowing mass outwardly, so that it reforms as discrete fibers with changed structures.

An apparatus which produces suitable conditions is a modified floss making machine, such as that described in a U.S. application Ser. No. 08/854,344 filed on May 12, 1997, entitled "Apparatus for Melt Spinning Feedstock Material having a Flow Restricting Ring". The content of that application is hereby incorporated by reference.

Typically, spinning is conducted at temperatures and speeds of about 180 to 250 degrees C. and 3,000 to 4,000 rpm, respectively.

Suitable spinner heads include that disclosed in U.S. Pat. No. 5,458,823, assigned to Applicants' assignee, which is hereby incorporated by reference.

Other useful apparatuses or processes which provide similar forces and temperature gradient conditions can be used.

The matrices used herein include a carrier, or feedstock, material which carrier material comprises at least one selected from materials which are capable of undergoing the physical and/or chemical changes associated with flash heat processing. Useful carriers include carbohydrates which become free-form particulates when flash heat processed. Saccharide-based carriers, including saccharides (i.e., sugars), polysaccharides and mixtures thereof can be used.

The feedstocks used in the invention can include carriers chosen from various classes of "sugars". "Sugars" are those substances which are based on simple crystalline mono- and di-saccharide structures, i.e., based on $C_5$ and $C_6$ sugar structures. They may include glucose, sucrose, fructose, lactose, maltose, pentose, arbinose, xylose, ribose, mannose, galactose, sorbose, dextrose and sugar alcohols, such as sorbitol, mannitol, xylitol, maltitol, isomalt, sucralose and the like and mixtures thereof. Sucrose is the preferred sugar.

Useful mixtures of carriers include the sugars listed above along with additional mono- di-, tri- and polysaccharides. Additional saccharides can be used in amounts of up to 50% by weight of the total sugar, preferably up to 30%, most preferably up to 20%.

Optionally, the polysaccharides can be used alone as carriers. Polysaccharide carriers include polydextrose and the like. Polydextrose is a non-sucrose, essentially non-nutritive, carbohydrate substitute. It can be prepared through polymerization of glucose in the presence of polycarboxylic acid catalysts and polyols. Generally, polydextrose is commercially available in three forms: polydextrose A and polydextrose K, which are powdered solids; and polydextrose N supplied as a 70% solution. Applicants incorporate by reference herein the contents of U.S. Pat. No. 5,501,858, which discusses polydextrose.

If other carrier materials are used, they are employed in combination with sugar and not as total replacement therefor. For example, maltodextrins may be employed. Maltodextrins include mixtures of carbohydrates resulting from the hydrolysis of a saccharide. They are solids having a dextrose equivalent (DE) of up to and including 65.

The carrier can also include maltooligo-saccharides produced by selective hydrolysis of corn starch. A general description of maltooligo-saccharides useful herein is set forth in co-owned U.S. Pat. Nos. 5,347,431 and 5,429,836, both incorporated herein by reference.

Applicants use the following systems of matrices, which systems are devoid of glycerine.

In the first system, xylitol is added to a mixture of saccharide-based carrier and one or more additional sugar alcohols, with sorbitol being favored as an added sugar alcohol. The carrier mix is flash-heat processed to provide a shearform floss having self-binding properties. Flosses made using sucrose, sorbitol and xylitol have been found to yield particularly effective self-binding properties. They exemplify "single floss" or "unifloss" systems.

The second system makes separate xylitol-containing binder flosses. The binder flosses ("binder portions") are combined with base flosses ("base portions"), which contain a different sugar alcohol and a saccharide. Preferably, the base floss contains sorbitol and sucrose, while the binder floss contains xylitol. These are termed "dual floss" systems.

The ingredients which increase cohesiveness and give self-binding properties preferably include sugar alcohols, such as sorbitol, xylitol, maltitol, mannitol and mixtures thereof, all of which form flosses. Other sugar alcohols, especially hygroscopic ones, are contemplated.

Xylitol and sorbitol are the preferred sugar alcohols. Effective amounts of xylitol in the flosses are between about 0.5% and 25%, and preferably about 10% by weight. Sorbitol is used in the flosses in amounts of about 0.5% to about 40%.

When sorbitol and xylitol are used, the ratio of sorbitol to xylitol is from about 1:0.1 to about 1:10.

In dual floss systems, about 20 to about 80%, preferably about 34%, of the total floss content is xylitol-containing, or binder, floss. Likewise, the sorbitol-containing, or base, floss may be about 20 to 80% of the total floss. In some "dual floss" embodiments, xylitol-containing flosses are first mixed with active ingredient(s), then mixed with sucrose/sorbitol flosses.

Regardless of the number of flosses, the total floss content preferably includes about 50 to about 85% sucrose, about 5 to about 20% sorbitol and about 5% to about 25% xylitol.

In some cases, flosses are used along with bio-affecting, or active, microspheres in the tableting process. Often, a xylitol-containing floss is added to microspheres of one or more active agents first and then a non-xylitol-containing floss is added. Typically, the weight ratio of total floss to microspheres is about 1:1. In these instances, about 5% to about 25% of the floss is xylitol.

Whereas prior art shearform matrices conventionally included a liquid binding additive such as glycerine, the present matrices do not. Instead, they get their enhanced cohesiveness, self-binding character and flowability directly from the matrix or feedstock ingredients and the processing used.

The amorphous shearform matrix of the present invention is preferably made from a feedstock which includes sucrose, sorbitol, and xylitol. As set forth in a co-assigned application (entitled "Fast Dissolving Comestible Units Formed under High Speed/High Pressure Conditions", Ser. No. 08/915, 067) filed concurrently herewith, these compositions promote recrystallization and tableting of the matrix-containing mixes to a level sufficient to provide particulate flowability for use in high speed and high pressure tableting equipment.

Applicants do not wish to be bound by a particular theory. However, they believe that a hygroscopic material must be present to provide good self-binding characteristics to the final matrices and the compositions containing them. The hygroscopic material must have a hygroscopicity which is substantially higher then that of the carrier carbohydrate (e.g., sucrose) and the non-xylitol sugar alcohol in order to produce and control the self-binding properties. Also, it must be capable of being flash-heat processed along with the carbohydrate component(s).

Applicants theorize that the hygroscopic material is initially present in the matrix in its amorphous state, but, due to its propensity to pick up moisture, it recrystallizes into a more crystalline structure. Due to the intimate contact between all components in the matrix, the recrystallization of one component can affect, to some extent, the characteristics of surrounding components and the properties of the matrix as a whole. When sufficient recrystallization has occurred in the hygroscopic material and the amorphous material as a whole, the matrix is such that, due the loss of some amorphous character, flowability is enhanced and conventional tableting machinery can be used.

The compositions to be processed into comestible units, or tablets, can contain conventional additives. Conventional quantities of these additives may be incorporated into one or more of the matrices or may be mixed therewith prior to tableting. Useful amounts of conventional additives range from about 0.01% to about 80% by weight, based on the weight of the matrices or formulations in which they are used. The quantities may vary from these amounts, depending on the functions of the additives and the characteristics desired in the matrices and/or the final tablet compositions.

Conventional tableting aids may be selected from a wide variety of materials such as lubricants, glidants, anti-caking agents and flow agents. For example, lubricants such as adipic acid, magnesium stearate, calcium stearate, zinc stearate, hydrogenated vegetable oils, sodium chloride, sterotex, polyoxyethylene, glyceryl monostearate, talc, polyethylene glycol, sodium benzoate, sodium lauryl sulfate, magnesium lauryl sulfate, sodium stearyl fumarate, light mineral oil and the like may be employed, with sodium stearyl fumarate preferred. Waxy fatty acid esters, such as glyceryl behenate, sold as "Compritol" products, can be used. Other useful commercial lubricants include "Stear-O-Wet" and "Myvatex TL". Mixtures are operable.

Lubricants are used in amounts ranging from about 0% to about 10%, with about 0.01% to about 5.0% typically used.

Glidants such as starch, talc, lactose, stearates, dibasic calcium phosphate, magnesium carbonate, magnesium oxide, calcium silicate, Cabosil, Syloid, and silicon dioxide aerogels may be employed.

Glidants are present in amounts ranging from about 0% to about 20%, with amounts of about 0.1% to about 5.0% being typical. Lactose, which may be a glidant or filler, can be added to the chopped floss at about 2% concentration to inhibit clumping.

The preformed matrices produced in accordance herewith may be rendered more crystalline by one or more of the following crystallizing techniques. The nature of the matrix feedstock determines whether the matrix is recrystallized after it is formed. Nonetheless, the terms "crystallization" and "recrystallization" are used interchangeably in the following discussion.

One technique for recrystallizing involves the use of crystallization enhancers. These are used after the floss has been formed, but before the floss-containing composition is tableted. Suitable crystallization enhancers include ethanol, polyvinylpyrrolidone, water (e.g. moisture), glycerine, radiant energy (e.g.., microwaves) and the like. Combinations can be used. When they are physical materials, typical amounts of these enhancers range from about 0.01% to about 10.0% by weight of the tablet composition.

Another technique relates to the use of crystallization modifiers. These crystallization modifiers are floss ingredients, used at levels of about 0.01% to about 20.0% by weight of the floss.

Surfactants are preferred crystallization modifiers. Other materials which are non-saccharide hydrophilic organic materials may also be used. Useful modifiers preferably have a hydrophilic to lipid balance (HLB) of about 6 or more. Such materials include, without limitation, anionic, cationic, and zwitterionic surfactants as well as neutral materials with suitable HLB values. Hydrophilic materials having polyethylene oxide linkages are effective. Those with molecular weights of at least about 200, preferably at least 400, are highly useful.

Crystallization modifiers useful herein include: lecithin, polyethylene glycol (PEG), propylene glycol (PPG), dextrose, the SPANS and TWEENS which are commercially available from ICI America, and the surface active agents known as "Carbowax". Generally, the polyoxyethylene sorbitan fatty acid esters called TWEENS, or combinations of such modifiers are used. Crystallization modifiers are usually incorporated into matrices in amounts of between about 0% and 10%.

Optionally, the matrices are allowed to recrystallize, with or without added crystallization modifiers, either before or after they are combined with the non-matrix component(s), e.g., the bio-affecting additive(s). When recrystallization occurs before tableting, the recrystallization level of the matrix generally reaches at least about 10%. The use of such partially recrystallized matrices leads to compositions that are free flowing and tabletable using conventional machines. U.S. Pat. No. 5,597,416 describes a process for recrystalizing in the presence of additives.

Methods for effecting the recrystallization of the matrices include: use of Tween 80 or other crystallization modifier(s) in the matrix premix; aging of the matrix for up to several weeks, contacting the matrix with sufficient moisture and heat to induce crystallization, and treating the floss or the floss-containing composition with ethanol or another crystallization enhancer. Combinations of these may be used.

When a surfactant, such as a Tween is used, about 0.001% to about 1.00% is included in the floss preblend as a crystallization modifier. Following preblending, the formulations are processed into flosses, then chopped and used, with or without additives, to make tablets. Mixtures of surfactants can be used.

Aging may be used to recrystallize the matrix or floss. The aging process involves a two-step process. First the matrix, which typically contains at least one crystallization modifier, is formed, chopped and allowed to stand in closed or sealed containers without fluidization or other agitation under ambient conditions, e.g., at room temperature and atmospheric pressure, for up to several days, preferably for about 1 to about 3 days. Later, the matrix is mixed, and optionally further chopped, with one or more other ingredients. The mix is then aged by allowing it to stand for an additional period of about 1 to about 3 days. Generally, the two-step aging process takes a total of about one week, with periods of about 4 to about 5 days being typical.

The flosses may also be recrystallized by subjecting them to increased heat and moisture. This process is similar to aging, but involves shorter periods of time. Using a fluidized bed apparatus or other suitable device, chopped floss is fluidized while heating, at ambient humidity and pressure, to a temperature of about 25° C. to about 50° C. Generally, the temperature must be monitored to minimize the floss particles clumping during this operation. If any clumping occurs, the floss particles must be sieved before being further processed into tablets. Heating times of about 5 to about 30 minutes are typical.

When ethanol is used as a crystallization enhancer it is used in amounts, based upon the weight of the matrix, of about 0.1% to about 10%, with amounts of about 0.5% to about 8.0% being very effective. The preformed matrix is contacted with ethanol. Excess ethanol is evaporated by drying for about an hour at about 85° F. to about 100° F., with 95° F. being highly useful. The drying step is carried out using tray drying, a jacketed mixer or other suitable method. Following ethanol treatment, the matrix becomes partially recrystallized on standing for a period ranging from about a few hours up to several weeks. When the floss is about 10 to about 30% recrystallized, it is tableted after blending with other ingredients. The tableting compositions flow readily and are cohesive.

Recrystallization of the matrix may take place in the presence of one or more bio-affecting agents or other additives.

Recrystallization of the matrix can be monitored by measuring the transmittance of polarized light therethrough or by the use of a scanning electron microscope. Amorphous floss or shearform matrix does not transmit polarized light and appears black in the light microscope when viewed with polarized light. Using bright field microscopy or the scanning electron microscope, the surface of the floss appears very smooth. In this condition, it is 0% recrystallized. That is, the floss is 100% amorphous.

Recrystallization of amorphous matrix starts at the surface of the mass and can be modified, e.g., accelerated, by the presence of crystallization modifiers, as well as moisture. When TWEENS assist the recrystallization, initiation of recrystallization is evidenced by a birefringence observed on the surface of the shearform matrix (floss) as viewed with polarized light. There are faint points of light riddled throughout the matrix' surface. When birefringence appears, recrystallization has begun. At this stage, recrystallization is between about 1% and 5%.

As recrystallizatiion proceeds, the birefringence on the surface of the matrix grows continually stronger and appears brighter. The points of light grow in size, number and intensity, seeming to almost connect. Using bright field or scanning electron microscopy, the surface of the matrix appears wrinkled. At this point, about 5 to 10% recrystallization has occurred.

Surfactant (e.g., TWEEN 80) droplets become entrapped within the matrix. These droplets are obscured as recrystallization proceeds. As long as they are visible, the floss is generally not more than about 10% to 20% recrystallized. When they are no longer observable, the extent of recrystallization is no more than about 50%.

The recrystallization of the matrix results in reduction of the total volume of material. Ordered assays of molecules take up less space than disordered arrays. Since recrystallization begins at the surface of the floss, a crust is formed which maintains the size and shape of the floss. There is an increase in the total free volume space within the floss as recrystallization nears completion, which manifests itself as a void inside the floss. This is evidenced by a darkened central cavity in light microscopy and a hollow interior in scanning electron microscopy. At this stage, the floss is believed to be about 50% to about 75% recrystallized.

The intensity of transmitted polarized light increases as the floss becomes more crystalline. The polarized light can be measured by a photon detector and assigned a value against calculated standards on a gray-scale.

The final observable event in the recrystallization of floss is the appearance of fine, "cat whisker-like" needles and tiny blades which grow and project from the surface of the floss. These fine crystals, believed to be sorbitol (cat whiskers) and xylitol (blades), literally cover the floss like a blanket of fuzz. These features can be easily recognized by both light and electron microscopes. Their appearance indicates the final stage of recrystallization. The floss is now 100% recrystallized, i.e., substantially non-amorphous.

The matrix portions of the tablettable composition are typically formed via flash-heat processing into a floss. The strands of the floss are macerated or chopped into rods for further processing. The rods of chopped floss have lengths of about 50 to about 500 microns.

When active agents, such as bio-affecting agents, are added, they are often added in the form of spheroidal particles, and generally as uniform microspheres. Suitable microspheres and other spheroidal particles can be made by "liquiflash" processes.

"Liquiflash" processing involves the use of heat and pressure to reduce the feedstock to a condition in which resistance to flow, e.g., viscosity, which impedes the propensity to form liquid droplets, is eliminated. In this condition, the mass has become liquid or "liquiform". Once all resistance to flow is gone, shear force is applied to the feedstock until discrete particles separate from the mass. The particles, called "shearlite" particles, have a size and shape influenced only by natural mass separation of the flowing feedstock. U.S. Pat. No. 5,458,823 and U.S. application Ser. No. 08/330,412, filed Oct. 28, 1994, both incorporated herein by reference, show processes and devices for such processing.

The inventive compositions may include one or more active ingredients, such as bio-affecting agents. These are typically prescription or over the counter medications.

The bio-affecting agent used may be selected from a broad range of drug, therapeutic or prophylactic materials. Representative classes of drugs include those in the following therapeutic categories: ace-inhibitors; anti-anginal drugs; anti-arrythmia agents; antiasthmatics; anticholesterolemics; anticonvulsants; antidepressants; antidiarrheal preparations; antihistamines; antihypertensives; anti-infectives; anti-inflammatories; antilipid agents; antimaniacs; antinauseants; antistroke agents; antithyroid preparations; anabolic drugs; antiparasitics; antipsychotics; antipyretics; antispasmodics; antithrombotics; anxiolytic agents; appetite stimulants; appetite suppressants; beta-blocking agents; bronchodilators; cardiovascular agents; cerebral dilators; chelating agents; cholecystekinin antagonists; chemotherapeutic agents; cognition activators; contraceptives; coronary dilators; cough suppressants' decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; laxatives; migraine treatments; mineral supplements; mucolytics, narcotics; neuroleptics; neuromuscular drugs; non-steroidal anti-inflammatories (NSAIDs); nutritional additives; peripheral vasodilators; polypeptides; prostaglandins; psychotropics; renin inhibitors; respiratory stimulants; steroids; stimulants; sympatholytics; thyroid preparations; tranquilizers; uterine relaxants; vaginal preparations; vasoconstrictors; vertigo agents; vitamins; wound healing agents; and others.

Bio-affecting agents which may be used in the invention include: acetaminophen; acetic acid; acetylsalicylic acid, including its buffered forms; albuterol and its sulfate; alcohol; alkaline phosphatase; allantoin; aloe; aluminum acetate, carbonate, chlorohydrate and hydroxide; alprozolam; amino acids; aminobenzoic acid; amoxicillin; ampicillin; amsacrine; amsalog; anethole; ascorbic acid; aspartame; atenolol; bacitracin; balsam peru; BCNU (carmustine); beclomethasone diproprionate; benzocaine; benzoic acid; benzophenones; benzoyl peroxide; bethanechol; biotin; bisacodyl; bomyl acetate; bromopheniramine maleate; buspirone; caffeine; calamine; calcium carbonate, casinate and hydroxide; camphor; captopril; cascara sagrada; castor oil; cefaclor; cefadroxil; cephalexin; cetyl alcohol; cetylpyridinium chloride; chelated minerals; chloramphenicol; chlorcyclizine hydrochloride; chlorhexidine gluconate; chloroxylenol; chloropentostatin; chlorpheniramine maleate; cholestyramine resin; choline bitartrate; chondrogenic stimulating protein; cimetidine and its hydrochloride; cinnamedrine hydrochloride; citalopram; citric acid; clarithromycin; clonidine and its hydrochloride salt; clorfibrate; cocoa butter; cod liver oil; codeine and codeine phosphate; cortisone acetate; ciprofloxacin HCl; cyanocobalamin; cyclizine hydrochloride; danthron; dexbromopheniramine maleate; dextromethorphan hydrobromide; diazepam; dibucaine; diclofenac sodium; digoxin; diltiazem; dimethicone; dioxybenzone; diphenhydramine and its citrate;

diphenhydramine hydrochloride; docusate calcium, potassium, and sodium; doxycycline hydrate; doxylamine succinate; efaroxan; enalapril; enoxacin; erythromycin; estropipate; ethinyl estradiol; ephedrine; epinephrine bitartrate; erythropoietin; eucalyptol; famotidine; ferrous fumarate, gluconate and sulfate; fluoxetine and its hydrochloride; 5-fluorouracil (5-FU); flurbiprofen; folic acid; fosphenytoin; furosemide; gabapentan; gentamicin; gemfibrozil; glipizide; glycerine; glyceryl stearate; griseofulvin; growth hormone; guafenesin; hexylresorcinol; hydrochlorothiazide; hydrocodone bitartrate; hydrocortisone and its acetate; 8-hydroxyquinoline sulfate; ibuprofen; indomethacin; inositol; insulin; iodine; ipecac; iron; isosorbide and its mono- and dinitrates; isoxicam; ketamine; kaolin; lactic acid; lanolin; lecithin; leuprolide acetate; lidocaine and its hydrochloride salt; lifinopril; liotrix; loratadine; lovastatin; luteinizing hormore; LHRH (lutenizing hormone replacement hormone); magnesium carbonate, hydroxide, salicylate, and trisilicate; mefenamic acid; meclofenamic acid; meclofenamate sodium; medroxyprogesterone acetate; methenamine mandelate; menthol; meperidine hydrochloride; metaproterenol sulfate; methyl nicotinate; methyl salicylate; methyl cellulose; methsuximide; metronidazole and its hydrochloride; metoprotol tartrate; miconazole nitrate; mineral oil; minoxidil; morphine; naproxen and its sodium salt; nifedipine; neomycin sulfate; niacin; niacinamide; nicotine; nicotinamide; nitroglycerine; nonoxynol-9; norethindrone and its acetate; nystatin; octoxynol; octoxynol-9; octyl dimethyl PABA; octyl methoxycinnamate; omega-3 polyunsaturated fatty acids; omeprazole; ondansetron; oxolinic acid; oxybenzone; oxtriphylline; para-aminobenzoic acid (PABA); padimate-O; paramethadione; pentastatin; peppermint oil; pentaerythritol tetranitrate; pentobarbital sodium; pheniramine maleate; phenobarbital; phenol; phenolphthalein; phenylephrine hydrochloride; phenylpropanolamine and its hydrochloride salt; phenytoin; phenelzine sulfate; pirmenol; piroxicam; polymicin B sulfate; potassium chloride and nitrate; prazepam; procainamide hydrochloride; procaterol; proxephene and its HCl salt; propoxyphene napsylate; pramiracetin; pramoxine and its hydrochloride salt; propanolol HCl; pseudoephedrine hydrochoride and sulfate; pyridoxine; quinapril; quinidine gluconate and sulfate; quinestrol; ralitoline; ranitadine; resorcinol; riboflavin; salicylic acid; sesame oil; shark liver oil; simethicone; sodium bicarbonate, citrate, and fluoride; sodium monofluorophosphate; sucralfate; sulfanethoxazole; sulfasalazine; sulfur; tacrine and its HCl salt; theophylline; terfinidine; thioperidone; trimetrexate; triazolam; timolol maleate; tretinoin; tetracycline hydrochloride; tolmetin; tolnaftate; triclosan; tripolidine hydrochloride; undecylenic acid; vancomycin; verapamil HCl; vidaribine phosphate; vitamins A, B, C, D, $B_1$, $B_2$, $B_6$, $B_{12}$, E, and K; witch hazel; xylometazoline hydrochloride; zinc; zinc sulfate; zinc undecylenate. Mixtures and pharmaceutically acceptable salts of these and other actives can be used.

One group of preferred active ingredients are antacids, $H_2$-antagonists and analgesics.

Antacids dosages can be prepared using ingredients such as: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, calcium carbonate, calcium phosphate, citrate ion (acid or salt), amino acetic acid, hydrate of magnesium aluminum sulfate, magaldrate, magnesium aluminosilicate, magnesium carbonate, magnesium glycinate, magnesium hydroxide, magnesium oxide, magnesium trisilicate, milk solids, aluminum mono- or di-basic calcium phosphate, tricalcium phosphate, potassium bicarbonate, sodium tartrate, sodium bicarbonate, magnesium aluminosilicates, tartaric acids and salts, and the like. Mixtures are operable. Moreover, antacids can be used in combination with $H_2$-antagonists.

Chewable antacid compositions which dissolve quickly can be made using the compositions of the invention.

Preferred analgesics include aspirin, acetaminophen, ibuprofen, and acetaminophen plus caffeine.

Other useful active ingredients include antidiarrheals such as IMMODIUM AD; antihistamines; antitussives; decongestants; vitamins and breath fresheners. Also contemplated are anxiolytics such as XANAX; antipsychotics such as CLOZARIL and HALDOL; non-steroidal antiinflammatories, such as VOLTAREN AND LODINE; antihistamines such as SELDANE, HISMANAL, RELAFEN and TAVIST; antiemetics such as KYTRIL and CESAMET; bronchodilators such as BENTOLIN, PROVENTIL; antidepressants such as PROZAC, ZOLOFT, and PAXIL; antimigraine agents such as IMIGRAN; ace-inhibitors such as VASOTEC, CAPOTEN AND ZESTRIL; anti-Alzheimers agents such as NICERGOLINE; and $Ca^{II}$-antagonists such as PROCARDIA, ADALAT AND CALAN.

$H_2$-antagonists contemplated include cimetidine, ranitidine hydrochloride, famotidine, nizatidine, ebrotidine, mefentidine, roxatidine, pisatidine and aceroxatidine.

Other ingredients which may be included are fillers, fragrances, dyes, flavors, sweeteners (both artificial and natural), and other conventional tablet additives.

For example, fillers may be used to increase the bulk of the tablet. Some of the commonly used fillers are calcium sulfate, both di- and tri-basic; starch; calcium carbonate; microcrystalline cellulose; modified starches, lactose, sucrose; mannitol and sorbitol.

Flavors may be chosen from natural and synthetic flavoring liquids. An illustrative list of such agents includes volatile oils, synthetic flavor oils, flavoring aromatics, oils, liquids, oleoresins and extracts derived from plants, leaves, flowers, fruits, stems and combinations thereof. A non-limiting representative list of these includes citric oils, such a lemon, orange, grape, lime and grapefruit an fruit essences, including apple, pear, peach, grape, strawberry, raspberry, cherry, plum, pineapple, apricot, or other fruit flavors.

Other useful flavorings include aldehydes and esters, such as benzaldehyde (cherry, almond); citral, i.e., alpha-citral (lemon, lime); neral, i.e., beta-citral (lemon, lime); decanal (orange, lemon); aldehyde C-8 (citrus fruits); aldehyde C-9 (citrus fruits); aldehyde C-12 (citrus fruits); tolyl aldehyde (cherry, almond); 2,6-dimethyloctanal (green fruit); 2-dodedenal (citrus, mandarin); mixtures thereof and the like.

The sweeteners may be chosen from the following non-limiting list: glucose (corn syrup), dextrose, invert sugar, fructose, and mixtures thereof (when not used as a carrier); saccharin and its various salts, such as the sodium salt; dipeptide sweeteners such as aspartame; dihydro-chalcone compounds, glycyrrhizin; Stevia Rebaudiana (Stevioside); chloro derivatives of sucrose such as sucralose; and sugar alcohols such as sorbitol, mannitol, xylitol, and the like. Also contemplated are hydrogenated starch hydrolysates and the synthetic sweeteners such as 3,6-dihydro-6-methyl-1-1-1,2,3-oxathiazin-4-one-2,2-dioxide, particularly the potassium salt (acesulfame-K), and sodium and calcium salts thereof. Other sweeteners may also be used.

Some embodiments include an effervescent disintegration agent to aid in masking the objectional taste of active ingredients, such as vitamins, medicines and/or minerals, etc. The positive organoleptic sensation achieved by the effervescent action in the mouth, as well as the texture, speed and sensation of disintegration, aid in masking undesirable flavor notes.

"Effervescent" refers to those agents which evolve gas. The gas- or bubble-generating action is often the result of the reaction of a soluble acid source and a carbonate source. The reaction of these two general classes of compounds produces carbon dioxide gas upon contact with water in saliva. Useful acids include: citric, tartaric, malic, fumaric, adipic, succinic and acid salts and anhydrides thereof. Acid salts may also include sodium dihydrogen phosphate, disodium dihydrogen pyrophosphate, acid citrate salts and sodium acid sulfite. While the food acids can be those indicated above, acid anhydrides of the above-described acids may also be used. Carbonate sources include dry solid carbonate and bicarbonate salts such as sodium bicarbonate, sodium carbonate, potassium bicarbonate and potassium carbonate, magnesium carbonate and sodium sesquicarbonate, sodium glycine carbonate, L-lysine carbonate, arginine carbonate and amorphous calcium carbonate. Mixtures of various acid and carbonate sources, as well as other sources of effervescence, can be used.

The effervescent agent can be included in at least three different ways. The first method includes incorporating the entire effervescent agent in the feedstock which is used to form the shearform product. The second involves adding the agent to an already formed shearform matrix. The third method incorporates one portion of the agent in the shearform matrix and adds another portion after formation of the matrix material. The artisan can determine the best way to use the agent for its effervescent properties.

Other ingredients include binders which contribute to the ease of formation and general quality of the tablet. Binders include starches, pregelatinized starches, gelatin, polyvinylpyrrolidone, methylcellose, sodium carboxymethylcellulose, ethylcellulose, polyacrylamides, polyvinyloxoazolidone and polyvinylalcohols.

Color additives can be used in preparing tablets. Such color additives include food, drug and cosmetic colors (FD&C), drug and cosmetic colors (D&C) or external drug and cosmetic colors (Ext. D&C). These colors are dyes, lakes, and certain natural and derived colorants. Useful lakes include dyes absorbed on aluminum hydroxide or other suitable carriers.

An optional feature involves microspheres which are components of substrate/coating systems. The substrate can be a non-active ingredient, such as a saccharide-based material, or it can be an active or a combination of actives. In one embodiment, the substrates are sugar shearlite particles having active agents coated thereon. The coating may include other types of coating materials, e.g., coloring agents. Additional coatings can be used.

Other useful substrate/coating systems employ substrates which are shearlite particles of one or more actives. Coatings thereon can contain saccharides and other ingredients.

Controlled release coatings, e.g., sustained release coatings, are among the preferred types of coatings for use in dosage forms which include bio-affecting agents.

Using the invention, strong, highly attractive dosage units, e.g, tablets, can be produced having textures and internal structures which are relatively open to solubilization. Applicants' compositions are intended genrally formed into tablets at pressures of from about 500 up to about 6,000 psi. These tablets have initial hardness values of about 0.5 to about 5.0 lbs.

The following non-limiting examples illustrate the invention.

EXAMPLE I

Ibuprofen Microspheres

Ibuprofen was processed into spheres as follows:

An ibuprofen powder feedstock was fed to a 5-inch spinning head disclosed in a U.S. application Ser. No. 08/847,215 filed on Jun. 13, 1997, entitled "A Spinner Head having Flow Restricting Inserts". The head was rotated at about 3600 rpm while the heating elements were raised to a temperature which produced the liquiflash conditions. The feedstock also contained 10% Compritol 888 ATO and 2% Gelucire 50/13. (Compritol 888 ATO is glycerol behenate NF, a lipophilic additive from Gattefosse S. A., a French company. Gelucire, a polyethylene glycol 32 glyceryl ester solubility enhancer, is also available from Gattefosse.)

After exiting the spinning head, the material was permitted to free fall a distance of from 6 to 8 feet below the head. The product consists of spheres having a highly consistent particle size, with diameters ranging from about 50 to 200 microns.

The product was subjected to testing to determine the time required for dissolution of the active ingredient. The monograph is provided by the U.S. Pharmacopeial Convention, Inc. in the U.S. Pharmaceopoeial National formulary Monograph for Ibuprofen Dissolution Study, U.S. 23 NF 18, page 786 (1995). At a composition level of 88% ibuprofen, the time for dissolution of most of the ibuprofen was about 15 minutes. Virtually total dissolution occurred at around 20 to 25 minutes. These results show high predictability for delivery using these microspheres.

EXAMPLE II

Acetaminophen Microspheres

In this example, acetaminophen was processed using a 60 mesh screen positioned in serpentine fashion between heating elements. Acetaminophen powder (melting point 169°–170.5° C.) was fed to a spinning head run at about 3600 rpm. While the feedstock was subjected to centrifugal force, the temperature was raised until the acetaminophen powder was reduced to liquiform. The force generated by the spinning head expelled acetaminophen out of the spinner head, and impelled it through the 60 mesh screen. The product was permitted to free fall below the head, a distance of about 6 to 8 feet.

Fine spheres, all smaller than about 420 microns in diameter, were formed. 4.33 kilograms of the spheres passed through a 40 mesh screen and 1.39 kilograms were retained.

EXAMPLE III

Tablet Composition containing 10% Xylitol

A. Preparation of Sucrose/Sorbitol Base Floss

The base floss was prepared from a mixture of 84.75 parts sucrose, 15.0 parts sorbitol, and 0.25 parts of TWEEN 80. The mix was flash flow processed in a device described in U.S. application Ser. No. 08/854,344. Two kilograms of this material was spun under ambient conditions of 60° F. and 35% relative humidity. Spinning was conducted at 3600 rpm (60Hz). The spun floss was collected and chopped in a mixer for about 45 seconds.

B. Preparation of Xylitol/Sucrose/Sorbitol Binder Floss

A mixture of 74.75 parts of sucrose, 15 parts xylitol, 10 parts sorbitol and 0.25 parts TWEEN 80 was prepared. Two kilograms of this material was spun into a floss under ambient conditions of 67° F. and 40% relative humidity at 3600 rpm (60Hz) using a 5 inch plate head as described above and chopped in a high shear mixer/chopper for 0.5 minutes.

357.6 grams of acetaminophen (APAP) beads made by the process described in Example II were placed in a Hobart blender bowl. Chopped binder floss (72.0 grams, sieved through 20 mesh) was added to the beads in the Hobart bowl and mixed for 2 minutes. The mix passed through 20 mesh sieve after mixing. 272.0 grams of sucrose/sorbitol base floss was added in 25% increments. With the last 25% increment, flavors (1.8 grams of citric acid, 1.983 grams of Alpine creme, 1.8 grams of lemon juice, and 4.82 grams of aspartame) were added. Each addition was mixed for 30 seconds. This mixture was further blended. The flowability of the tablet blend was measured, resulting in an angle of rupture of 80° and an angle or repose of 55°. This preparation flowed freely. To this mixture was added 0.1% of Syloid. The final blend was tableted on a Stokes D-3 tablet press at settings which provided a 1.2 g. tablet with an initial hardness of 1 lb.

The ingredients are summarized as follows:

| Saccharide (Base) Floss | |
|---|---|
| Sucrose | 84.75 g |
| Sorbitol | 15.00 g |
| TWEEN 80 | 0.25 g |
| Xylitol (Binder) Floss | |
| Sucrose | 74.75 g |
| Xylitol | 15.00 |
| Sorbitol | 10.00 g |
| TWEEN 80 | 0.25 g |
| Tablet Composition - 10% Xylitol in Total Composition | |
| Citric Acid | 1.80 g |
| Alpine creme | 1.80 g |
| Lemon juice | 1.80 g |
| Aspartame | 4.80 g |
| APAP | 340.9 g |
| Chopped floss* | 368.9 g |
| | 720.0 g (total) |

*The floss contained 15% sorbitol-containing base floss and 85% xylitol-containing binder floss.

EXAMPLE IV

Preparation of 16% Xylitol Composition

Using the flosses and mixing procedures of Example III, a 16% xylitol composition was prepared and tableted at 80 and 1 00psi with 0.3 seconds dwell time.

The tablet composition was:

| Citric acid | 1.81 g |
|---|---|
| Alpine creme | 1.83 g |

-continued

| Lemon Juice | 1.80 g |
|---|---|
| Aspartame | 4.84 g |
| APAP | 340.00 g |
| Chopped floss** | 368.00 g |
| | 720.00 g (total) |

**The chopped floss had a 1:0.57 ratio of sorbitol base floss to xylitol binder floss.

EXAMPLE V

Preparations with 25%, 34% and 100% Xylitol Floss in Final Blend

This example illustrates tablet compositions containing varying amounts of xylitol-containing (binder) floss.

| Sorbitol (Base) Floss | |
|---|---|
| Sucrose | 84.75 g |
| Sorbitol | 15.00 g |
| TWEEN 80 | 0.25 g |

2 kilograms of the material was spun under ambient conditions of 66° F. and 38% relative humidity. It was spun at 3600 rpm (60 Hz), as described in Example III, and chopped.

| Xylitol (Binder) Floss | |
|---|---|
| Sucrose | 69.75 g |
| Xylitopl | 25.00 g |
| Sorbitol | 10.00 g |
| TWEEN 80 | 0.25 g |

2 kg of this mix was spun at 67°–68° F., 3600 rpm (60 Hz) on a 5 inch head and chopped.

A. 25% Xylitol Floss

A 25% xylitol floss containing preparation was made using the following ingredients:

| Citric acid | 1.83 g |
|---|---|
| Alpine creme | 1.80 g |
| Lemon juice | 1.82 g |
| Aspartame | 4.84 g |
| APAP | 353.88 g |
| Sorbitol floss | 61.12 g |
| Xylitol floss | 294.80 g |
| Cab-o-sil | 0.36 g |
| | 720.43 g (total) |

The APAP and 55% of the xylitol binder floss (sieved through a 20 mesh sieve) were mixed. The remaining binder floss and the sorbitol/sucrose floss were mixed by hand and sieved through a 20 mesh sieve. This mix was added in 25% increments to binder floss/APAP mixture. With the last increment, the citric acid, Alpine creme, lemon juice and aspartame were added.

From this mixture, 10 grams were removed and mixed with the Cab-o-sil end. The bulk tableting blend was mixed for 30 seconds, then was tableted on a Stokes D-3 tablet press using the settings from Example III.

B. 34% Xylitol Floss

The 34% formulation was made from the following ingredients:

| | |
|---|---|
| Citric acid | 1.82 g |
| Alpine creme | 1.81 g |
| Lemon juice | 1.81 g |
| Aspartame | 4.80 g |
| APAP | 353.88 g |
| Sorbitol floss | 111.12 g |
| Xylitol floss | 244.80 g |
| Cabosil | 0.36 g |
| | 720.00 g (total) |

Using procedures similar to those employed in Example III, the formulation was tableted.

C. 100% Xylitol Floss

The following formulation of 100% xylitol binder floss was prepared:

| | |
|---|---|
| Citric acid | 1.82 g |
| Alpine creme | 1.81 g |
| Lemon juice | 1.81 g |
| Aspartame | 4.80 g |
| APAP | 353.88 g |
| Cabosil | 0.36 g |
| Xylitol floss | 355.92 g |
| | 720.4 g (total) |

Using procedures similar to those in Ezample III, the blend was mixed and tableted.

EXAMPLE VI

Unifloss

Using a procedure similar to that of Example I, ibuprofen microspheres were made from a formulation containing 88% ibuprofen, 10% Compritol and 2% Gelucire.

Using a process similar to that described in Example IIIB, a floss was made from the following composition: 78.25% sucrose, 11.0% sorbitol, 10.0% xylitol and 0.75%TWEEN.

The microspheres and floss were then admixed used in the following composition:

| | |
|---|---|
| Microspheres | 34.4% |
| Floss | 62.7% |
| Citric acid | 0.7% |
| Lemon flavor | 0.4% |
| Whipped cream flavor | 0.3% |
| Syloid 244 FP | 0.5% |
| Sodium stearyl fumarate | 1.0% |

Using a Kilian T-200 press, 750 mg. tablets were pressed to a 2 lb. initial hardness.

EXAMPLE VII

Reduced Xylitol Floss

Using the procedure of Example I, ibuprofen microspheres were made from a formulation containing 88% ibuprofen, 10% Compritol and 2% Gelucire. Via a single floss process similar to that of Example VI, a floss was made from the following composition: 83.25% sucrose, 11.0% sorbitol, 5.0% xylitol and 0.75%TWEEN.

The microspheres and floss were used in the following composition:

| | |
|---|---|
| Microspheres | 34.4% |
| Floss | 62.7% |
| Citric acid | 0.7% |
| Lemon flavor | 0.4% |
| Whipped cream flavor | 0.3% |
| Syloid 244 FP | 0.5% |
| Sodium stearyl fumarate | 1.0% |

The ingredients were mixed and the mix was tableted using procedures as described in Example VI.

EXAMPLE VIII

Low Compression Tableting

Using the procedure described in Example VI, a floss was produced from the following composition:

| | |
|---|---|
| Sorbitol | 11.0% |
| Xylitol | 10.00% |
| Sucrose | 78.75% |
| TWEEN 80 | 0.25%. |

The floss was then combined with ibuprofen microspheres made in accordance with Example I as well as other tablet ingredients to make a tablet composition. The tablet composition was:

| | |
|---|---|
| Floss | 64.1% |
| Ibuprofen microspheres | 34.4% |
| Citric acid | 0.7% |
| Lemon flavor | 0.4% |
| Whipped cream flavor | 0.3% |
| CAB-O-SIL | 0.1% |

The mixture was tableted, at a rate of about 15,000 to 20,000 tablets per hour, using the low compression tableting apparatus described in Italian patent application No. B096A 000453, filed Sep. 11, 1996 and entitled "Meto Do E Macchina Per La Produzione Di Pasti Glie Di Polvere Medicinale" ("Method and Machine for Tablet Production of Medicine Powder"). The disclosure of that application is hereby incorporated by reference. The resultant tablets weighed 750 mg and had initial hardness values of 1 lb.

U.S. applications Ser. No. 08/437,300 and Ser. No. 08/438,239, both filed on May 9, 1995, now U.S. Pat. Nos. 5,653,926 and 5,662,849 respectively and U.S. Pat. No. 5,637,326, also incorporated herein by reference, describe various aspects of useful processes and machines.

There have been described what are presently believed to be the preferred embodiments of the invention. Those skilled in the art will realize that changes and modifications may be made thereto without departing from the spirit of the invention, and it is intended to claim all such changes and modifications as fall within the true scope of the invention.

We claim:

1. A glycerine-free shearform matrix having enhanced self-binding characteristics consisting essentially of at least one saccharide-based carrier and the sugar alcohols sorbitol and xylitol.

2. The matrix of claim 1 wherein the ratio of sorbitol to xylitol is about 1:0.1 to about 1:10.

3. The matrix of claim 1 wherein about 0.5% to about 25% by weight of xylitol is present.

4. The matrix of claim 1 wherein about 0.5% to about 40% by weight of sorbitol is present.

5. The matrix of claim 4 wherein the carrier is sucrose.

6. The matrix of claim 4 wherein the carrier is a polysaccharide.

7. The matrix of claim 1 prepared by combining a sorbitol-containing portion with a xylitol-containing portion.

8. A glycerine-free self-binding tabletable composition consisting essentially of:
   at least one bioaffecting agent; and
   a shearform-based carrier, sorbitol and xylitol in combination, wherein the xylitol and sorbitol are present in amounts effective to give the composition self-binding properties.

9. The composition of claim 8 wherein the carrier is sucrose.

10. The composition of claim 9 comprising:
    a shearform matrix which includes sucrose, sorbitol and xylitol in combination, wherein the ratio of sorbitol to xylitol is about 1: 0.1 to about 1:10.

11. The composition of claim 10 wherein said agent is in the form of microspheres.

12. The composition of claim 11 wherein the bio-affecting agent is selected from the group consisting of acetaminophen, ibuprofen, aspirin and mixtures thereof.

13. The composition of claim 12 further including at least one additive selected from lubricants and other excipients.

14. The composition of claim 13 wherein the other excipient is selected from: flavors, fragrances, colorants, glidants, sweeteners, crystallization modifiers and fillers.

15. The composition of claim 14 wherein the lubricant is sodium stearyl fumarate.

16. The composition of claim 15 wherein the other excipient is lactose.

17. The composition of claim 15 containing: 34.4% ibuprofen microspheres, 62.7% sugar/sorbitol/xylitol matrix, 0.7% citric acid, 0.4% lemon flavor, 0.3% whipped cream flavor, 0.5% silicon dioxide, and 1.0% sodium stearyl fumarate.

18. The composition of claim 17 additionally containing 2.0% lactose.

19. The composition of claim 17 wherein the ibuprofen microspheres are produced from a composition containing: 88% ibuprofen, 10% glyceryl behenate, and 2% polyethylene glycol glyceryl ester.

20. The composition of claim 19 wherein the matrix contains: 78.25% sucrose, 11.0% sorbitol, 10.0% xylitol, and 0.75% polyoxyethylene sorbitan fatty acid ester.

21. The composition of claim 19 wherein the matrix contains: 83.25% sucrose, 11.0% sorbitol, 5.0% xylitol and 0.75% polyoxyethylene sorbitan fatty acid ester.

22. A self-binding tabletable composition comprising:
    (i) a first shearform carrier matrix containing at least one saccharide-based carrier and at least one sugar alcohol; and
    (ii) a second shearform binder matrix containing xylitol, wherein the sugar alcohol(s) in (i) and the xylitol in (ii) are present in amounts sufficient to make the compositions self-binding.

23. The composition of claim 22 wherein (i) contains sorbitol.

24. The composition of claim 23 wherein said first shearform matrix and said second shearform matrix are present in amounts of about 80 to 20% and 20 to 80% by weight, respectively.

25. A method of enhancing the self-binding properties of a glycerine-free saccharide-based shearform matrix comprising the use of xylitol and one other sugar alcohol as feedstock ingredients.

26. The method of claim 25 wherein the other sugar alcohol is sorbitol.

27. The method of claim 26 wherein the ratio of sorbitol to xylitol is about 1:0.1 to about 1:10.

28. A glycerine-free shearform matrix having enhanced self-binding characteristics made from a carrier consisting essentially of (a) a sugar, and (b) a blend of sorbitol and xylitol wherein the ratio of sorbitol to xylitol is about 1:0.1 to about 1:1.0.

29. The shearform matrix of claim 28 wherein (a) is selected from the group consisting of: sucrose and a polysaccharide.

30. The shearform matrix of claim 29 wherein (a) is sucrose.

* * * * *